United States Patent [19]

Yuhda et al.

[11] Patent Number: 5,108,506
[45] Date of Patent: Apr. 28, 1992

[54] DENTAL CEMENT HARDENED BY A CARBOXYL GROUP-MODIFIED SILICONE OIL AND A HARDENING ACCELERATOR

[75] Inventors: Sadayuki Yuhda, Suita; Masahiko Ueda, Neyagawa, both of Japan

[73] Assignee: Sankin Kogyo Kabushiki Kaisha, Osaka, Japan

[21] Appl. No.: 343,625

[22] Filed: Apr. 27, 1989

[51] Int. Cl.$^5$ .................. C09K 3/00; A61C 3/00; A61C 13/08
[52] U.S. Cl. ...................... 106/35; 433/208; 433/8; 433/226
[58] Field of Search ............. 106/35; 433/208, 8, 433/226; 523/122

[56] References Cited

U.S. PATENT DOCUMENTS

| | | | |
|---|---|---|---|
| 4,007,153 | 2/1977 | Smith | 524/783 |
| 4,499,251 | 2/1985 | Omura et al. | 526/278 |
| 4,515,930 | 5/1985 | Omura et al. | 106/35 |
| 4,650,847 | 3/1987 | Omura et al. | 106/35 |

FOREIGN PATENT DOCUMENTS 2612554 10/1976 Fed. Rep. of Germany.
75908 5/1982 Japan.

OTHER PUBLICATIONS

New Riverside University Dictionary, 1984 p. 634.

*Primary Examiner*—Prince Willis, Jr.
*Assistant Examiner*—J. Silbermann
*Attorney, Agent, or Firm*—Oblon, Spivak, McClelland, Maier & Neustadt

[57] ABSTRACT

A dental cement having a composition consisting essentially of a hardening liquid, a hardening accelerator, wherein the hardening liquid consists essentially of carboxyl-modified silicone oil.

14 Claims, No Drawings

DENTAL CEMENT HARDENED BY A CARBOXYL GROUP-MODIFIED SILICONE OIL AND A HARDENING ACCELERATOR

BACKGROUND OF THE INVENTION

The present invention relates to dental cements particularly used for restoration of teeth, root canal treatment and periodontal tissue treatment, and more particularly to dental cements for such use which sets in the treated parts without stimulating the dental pulps.

So far zinc phosphate cement, polycarboxylate cement, glass ionomer cement and others are known for dental use, and they are used for particular uses depending upon their properties.

The zinc phosphate cement containing zinc oxide and orthophosphoric acid is well known, and actually has been in wide use over a long period of time. Nowadays it finds many applications in dental treatments. This cement is prepared by mixing a powdery constituent consisting mainly of ZnO and an aqueous constituent consisting of orthophosphoric acid, phosphate and water. When they are mixed, they chemically react with each other to form a hydrate of zinc phosphate, which is considered to surround the zinc oxide particles and grow into a solid mass. The nature and properties of zinc phosphate cement are fully studied and known so that it provides no problem in handling. In fact the zinc phosphate cement in commerce is superior in the hardening action. However one of the disadvantages is that it tends to contract when it hardens, and another is that the surface is likely to dissolve when it is subjected to water. A further disadvantage is that the pH value of the cement decreases until it indicates strong acidity at the initial stage of mixing the powdery and aqueous constituents. If the highly acid cement is used for the dental treatments mentioned above, it is likely to stimulate the tooth pulps and damage the flesh. A considerable care must be taken not to damage the neighboring teeth when such a highly acid cement as zinc phosphate cement is used. It is recommended that varnishes and zinc oxide eugenol-base liners are used.

The polycarboxylate cement in commerce contains a 32 to 42% aqueous solution of polyacrylic acid having a molecular weight of 25,000 to 50,000 and a powdery constituent consisting mainly of ZnO and MgO. For use, the aqueous constituent and powdery constituent are mixed to form a zinc polyacrylate gel in which the unreacted zinc oxide particles are retained, and solidifies. Advantages of the polycarboxylate cement are (1) its strong bond to the enamel and dentin, and (2) that although the mixture likewise exhibits a stronger acidity than the zinc phosphate cement, the high acidity derives from the dissociation of acid but actually the acidity is not detrimentally high. In addition, it has a large molecular weight, so that there is no likelihood of seriously stimulating the tooth pulps. However the disadvantage is that the resulting solidity is lower than is with the zinc phosphate cement, so that the mass cannot withstand the biting pressure over a long period of time.

In order to solve the problem of the polyacrylate cement, glass ionomer cement is proposed, which contains a mixture of an aqueous solution consisting mainly of polyacrylate and a powdery constituent consisting mainly of $SiO_2$ and $Al_2O_3$. This cement is tough and strengthens the teeth owing to the fluoride release. Recently this property is highly appreciated, but, on the other hand, it has been found that at the initial stage the cement is apt to soften in the presence of water, and that it stimulates the dental roots.

In root canal treatments zinc oxide eugenol cement is widely used. However, it has the same drawbacks of stimulating the teeth and lacking compatibility with the tissues.

Accordingly, the present invention aims at overcoming the difficulties pointed out with respect to the known dental cements discussed above. Thus an object of the present invention is to provide a dental cement which does not substantially stimulate the tooth pulps.

A further object of the present invention is to provide a dental cement which is compatible with the

SUMMARY OF THE INVENTION

According to the present invention, there is provided a dental cement having a composition consisting essentially of a hardening liquid and a hardening accelerator, wherein the hardening liquid consists essentially of carboxyl-modified silicone oil.

Other objects and advantages of the present invention will become more apparent from the following detailed description, when taken in conjunction with each example which shows, for the purpose of illustration only, one embodiment in accordance with the present invention.

DETAILED DESCRIPTION OF THE INVENTION

The cement of the present invention consists essentially of a hardening liquid, and a hardening accelerator, and depending upon the applications, it may contain a hardening regulator and/or an aggregate. As the hardening liquid a carboxyl-modified silicone oil can be used as a main constituent, wherein it can occupy 50% or more of the total quantity, preferably 90% or more if an increased solidity is desired. 99% or more is most preferable. As carboxyl-modified silicone oils the following substances can be effectively used:

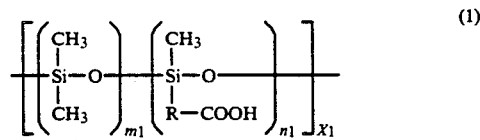

(1)

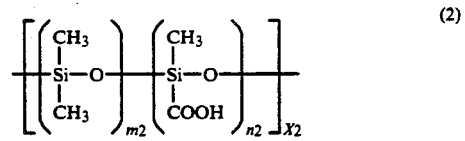

(2)

where $m_1$, $m_2$, $n_1$, $n_2$, $X_1$ and $X_2$ stand for identical or different integers. R means bivalent hydrocarbon residues.

The bivalent hydrocarbon residues indicated by R in the formula (1) are, for example, alkylene having 1 to 20 carbons such as methylene, ethylene, isopropylene, n-propylene, butylene, decene.

The hardening accelerator can be a metallic oxide such as ZnO, CaO, $Al_2O_3$ and MgO, and/or metallic hydroxides such as $Ca(OH)_2$, $Zn(OH)_2$ and $Mg(OH)_2$ can be used. The hardening accelerator is added singly or in combination.

Briefly stated, the dental cement according to the present invention utilizes the hardening action effected by the hardening liquid and the hardening accelerator for dental uses. When carboxyl-modified silicone oil and the metallic oxides and/or metallic hydroxides are mixed, they react with each other to present a gelative state, in which the cement sets or hardens with the core of the unreacted metallic oxide and metallic hydroxide. In this way the cement sets to effect the restoration of teeth and root canal treatment. Although it is not academically ascertained why the favorable result comes up, one approach indicates that the hardening derives from the chelation taking place between the carboxylic group in the carboxyl-modified silicone oil and the metals in the metallic oxide and/or the metallic hydroxide.

In the present invention a hardening regulator is added, which is selected from organic acids such as acetic acid, lactic acid, glycolic acid, citric acid, malic acid, maleic acid, fumaric acid, and inorganic acids such as hydrochloric acid, nitric acid and phosphoric acid. Without using these regulators the cement hardens relatively quickly, but if it is desired that the hardening speeds up, these substances are preferably added after they are mixed in an appropriate proportion. As the speed of the hardening increases, the treatment is finished in a shorter period of time, thereby lessening the pain involved in the treatment. This will be a blessing to the patients.

Particularly when the cement of the present invention is to be used for covering the tooth pulps or others, a hardening liquid, a hardening accelerator and a hardening regulator can be mixed in an appropriate proportion so as to satisfy the particular requirements. When the cement is used for root canal treatments, the important requirement is the confining ability and biological compatibility with the tissue rather than the strength of the mass.

In order to increase the biological compatibility an aggregate is added to the mixuture of the hardening liquid, the hardening accelerator and the hardening regulator. As the aggregate calcium phosphate compound is used, which is selected from hydroxy apatite, tricalcium phosphate and tetracalcium phosphate. Another advantage of the present invention is that the cement is well integrated to the teeth; particularly when the calcium-based aggregate mentioned above is added, the calcium enhances the integration of the cement to the teeth, and promotes the growth of new teeth because of its good biological compatibility.

EXAMPLE 1

The following liquid constituents and powdery constituents were prepared:

| The liquid constituents: | |
|---|---|
| carboxyl-modified silicone oil ("X-22-3715" manufactured by Sin'etsu Silicone Co., Ltd. carboxyl eqivalent: 600) | 99.95 parts |
| lactic acid | 0.05 parts |
| The powdery constituents: | |
| $Ca(OH)_2$ | 10 parts |
| tricalcium phosphate | 90 parts |

1.8 g of the powdery constituents and 1.0 g of the liquid constituent were mixed, and the properties thereof were examined, the results of which are shown in Table (1). For comparison, two commercial products were examined, the results of which are also shown in Table (1). One product is polyacrylic-acid base dental cement, branded "Apatite Rootsealer" (manufactured by Sankin Kogyo Industry Co., Ltd.) and the other is zinc-oxide-eugenol-based dental cement, branded "Canals" (manufactured by Showa Yakuhin kako Co., Ltd.). The tests were conducted in accordance with the Standard No. 57 of The American Dental Association (ADA).

TABLE (1)

| | ADA Standard | Example 1 | "Apatite Rootsealer" | "Canals" |
|---|---|---|---|---|
| Powder/Liquid Ratio (g/g) | — | 1.8/1.0 | 0.9/1.0 | 5.0/1.0 |
| Flow (mm) | 25< | 60 | 58 | 56 |
| Working Time (min) | — | 60 | 55 | 90 |
| Setting Time (min) | — | 90 | 150 | 90 |
| Film Thickness ($\mu$) | 50> | 15 | 35 | 13 |
| Solubility & Disintegration (%) | 3> | 0.155 | 1.705 | 0.072 |
| Dimensional Stability (%) | 1> | nil | −0.725 | −0.374 |

As is evident from the Table (1), the flow is satisfactory, and a sufficient working time is obtained. The setting time is relatively short, thereby lessening the pain inflicted upon the patients. The solubility in the mouth is also satisfactory. The cement of the invention was packed in the jaw of a Wistar rat, and any histological change with time was pathologically examined. However, no inflammation was discerned in the tissues. The cement did not stimulate the tissue and had high biological compatibility.

The Table (2) shows the results of Examples (2) to (7) in accordance with the ADA Standard No. 57 with respect to the flow, the working time and the setting time:

TABLE (2)

| | Examples | | | | | | |
|---|---|---|---|---|---|---|---|
| | 2 | 3 | 4 | 5 | 6 | 7 | 8 |
| Powder (%) | | | | | | | |
| calcium hydroxide | 0 | 0 | 0 | 0 | 0 | 5 | 10 |
| zince oxide | 100 | 50 | 100 | 40 | 40 | 0 | 30 |
| apatite hydroxide | 0 | 0 | 0 | 60 | 0 | 95 | 0 |
| tribasic calcium Phosphate | 0 | 50 | 0 | 0 | 60 | 0 | 60 |
| Liquid (%) | | | | | | | |
| Carboxyl- modified | (oil-1) 99 | (oil-1) 99.5 | (oil-2) 100 | (oil-2) 100 | (oil-2) 100 | (oil-3) 100 | (oil-4) 99.9 |

TABLE (2)-continued

|  | Examples | | | | | | |
| --- | --- | --- | --- | --- | --- | --- | --- |
|  | 2 | 3 | 4 | 5 | 6 | 7 | 8 |
| silicone oil |  |  |  |  |  |  |  |
| lactic acid | 1 | 0.5 | 0 | 0 | 0 | 0 | 0.1 |
| Powder/liquid ratio (g/g) | 2.0/1.0 | 3.0/1.0 | 2.5/1.0 | 2.5/1.0 | 3.0/1.0 | 2.0/1.0 | 2.0/1.0 |
| Flow (mm) | 40 | 55 | 40 | 60 | 50 | 30 | 28 |
| Working time (min) | 15 | 20 | 15 | 90 | 60 | 10 | 3 |
| Setting time (min) | 30 | 120 | 45 | 120 | 100 | 30 | 10 |

(Note)
Oil-1 is manufactured by Toray silicone Co. Ltd.
No. "555" (carboxyl equivalent: 350)
Oil-2 is manufactured by Toshiba Silicone Co., Ltd.
"XF42-711" (carboxyl equivalent: 670)
Oil-3 is manufactured by Shin'etsu Silicone Co. Ltd.
"X-22-3710" (carboxyl equivalent: 1250)
Oil-4 is manufactured by Shin'etsu Silicone Co. Ltd.
"X-22-3701E" (carboxyl equivalent: 3800)

As is evident from the foregoing description, the cement of the present invention contains carboxyl-modified silicone oil for a hardening liquid, thereby eliminating the possibility of stimulating the tooth pulps and enhancing the confining ability and the biological compatibility.

What is claimed is:

1. A dental cement consisting essentially of at least 50 wt. %, based on the constituents of the dental cement, of a carboxyl group-modified silicone oil as a hardening liquid which exhibits a hardening effect to dental surfaces and an effective amount of a hardening accelerator, wherein the hardening accelerator is a metallic oxide and/or a metallic hydroxide.

2. The dental cement as set forth in claim 1, wherein the carboxyl-modified silicone oil expressed by the formula:

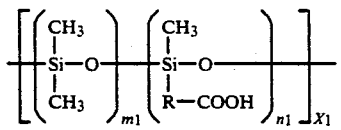

wherein $m_1$, $n_1$, and $X_1$ stand for identical or different positive integers and R is a divalent hydrocarbon radical.

3. A dental cement as set forth in claim 1, wherein the carboxyl-modified silicone oil is expressed by the formula:

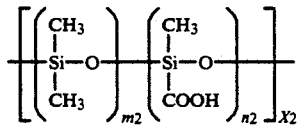

(2)

where $m_2$, $n_2$, and $X_2$ stand for identical or different positive integers.

4. A dental cement as set forth in claim 1, wherein the metallic oxide is one or more substances selected from the group consisting of ZnO, CaO, $Al_2O_3$ and MgO.

5. A dental cement as set forth in claim 1, wherein the metallic hydroxide is one or more substances selected from the group consisting of $Ca(OH)_2$, $Zn(OH)_2$ and $Mg(OH)_2$.

6. A dental cement as set forth in claim 1, further containing an effective amount of a hardening regulator.

7. A dental cement as set forth in claim 6, wherein the hardening regulator is an organic acid and/or an inorganic acid.

8. A dental cement as set forth in claim 7, wherein the organic acid is one or more substances selected from the group consisting of acetic acid, lactic acid, glycolic acid, citric acid, malic acid, maleic acid and fumaric acid.

9. A dental cement as set forth in claim 7, wherein the inorganic acid is one or more substances selected from the group consisting of hydrochloric acid, nitric acid and phosphoric acid.

10. A dental cement as set forth in claim 1 or 7, further containing an effective amount of an aggregate.

11. A dental cement as set forth in claim 10, wherein the aggregate is calcium phosphate.

12. A dental cement as set forth in claim 11, wherein the aggregate is one or more substance selected from the group consisting of hydroxy apatite, tricalcium phosphate and tetracalcium phosphate.

13. A method of lining teeth or capping pulp, comprising:
   applying the dental cement of claim 1 to tooth surfaces or tooth pulp.

14. A method for filling root canals of teeth, comprising:
   filling the root canals of teeth with the dental cement of claim 1.

* * * * *